United States Patent
Nielsen et al.

(10) Patent No.: US 10,174,346 B2
(45) Date of Patent: Jan. 8, 2019

(54) MICROORGANISMS ENGINEERED TO PRODUCE PHENOL AND ITS DERIVATIVES

(71) Applicants: David Nielsen, Tempe, AZ (US); Shawn Pugh, Mesa, AZ (US); Brian Thompson, Tempe, AZ (US)

(72) Inventors: David Nielsen, Tempe, AZ (US); Shawn Pugh, Mesa, AZ (US); Brian Thompson, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 209 days.

(21) Appl. No.: 14/908,967

(22) PCT Filed: Aug. 12, 2014

(86) PCT No.: PCT/US2014/050756
§ 371 (c)(1),
(2) Date: Jan. 29, 2016

(87) PCT Pub. No.: WO2015/031048
PCT Pub. Date: Mar. 5, 2015

(65) Prior Publication Data
US 2016/0160244 A1 Jun. 9, 2016

Related U.S. Application Data

(60) Provisional application No. 61/870,663, filed on Aug. 27, 2013.

(51) Int. Cl.
| | |
|---|---|
| C12P 1/04 | (2006.01) |
| C12P 5/00 | (2006.01) |
| C12P 17/00 | (2006.01) |
| C12P 7/22 | (2006.01) |
| C12N 9/88 | (2006.01) |
| C12N 9/90 | (2006.01) |
| C12P 7/44 | (2006.01) |

(52) U.S. Cl.
CPC ............ *C12P 7/22* (2013.01); *C12N 9/88* (2013.01); *C12N 9/90* (2013.01); *C12P 7/44* (2013.01)

(58) Field of Classification Search
CPC .......... C12P 5/0005; C12P 17/02; C12P 1/04; C12N 9/88
See application file for complete search history.

(56) References Cited

U.S. PATENT DOCUMENTS 3,660,235 A 5/1972 Okumura et al.
4,681,852 A 7/1987 Tribe

FOREIGN PATENT DOCUMENTS

| WO | 2012122333 | 9/2012 |
| WO | 2012122333 A1 | 9/2012 |
| WO | 2015031048 | 3/2015 |

OTHER PUBLICATIONS

Ozenberger et al., J. Bacteriology, 17(2), 775-782, 1989.*
Gaille et al., JBC, 278, 16893-16898, 2003.*
Gaille et al., JBC, 277, 21768-21775, 2002.*
Wierckx et al. 'Engineering of Solvent-Tolerant Pseudomonas putida S12 for Bioproduction of Phenol from Glucose,' Applied and Environmental Microbiology, Dec. 1, 2005 (Dec. 1, 2005), vol. 71, No. 12, pp. 8221-8227. entire document.
Krab-Husken, L. 'Production of Catechols: microbiology and technology. Thesis Wageningen University. The Netherlands- with Dutch summary. pp. 1-144. Aug. 19, 2002. Retrieved from the Internet<edepot.wur.nl/121336> on Nov. 18, 2014 (Nov. 18, 2014). entire document.
Balderas-Hernandez et al. 'Catechol biosynthesis from glucose in *Escherichia coli* anthranilate-overproducer strains by heterologous expression of anthranilate 1,2-dioxygenase from Pseudomonas aeruginosa PA01,' Microbial Cell Factories, Oct. 4, 2014 (Oct. 4, 2014). vol. 13, pp. 1-11. entire document.
Zhang et al. 'Synthetic biology applications in industrial microbiology'. Frontires in Microbiology, Aug. 26, 2014 (Aug. 26, 2014), vol. 5, Article 451, pp. 1-2. entire document.
Qi et al., Functional expression of prokaryotic and eukaryotic genes in *Escherichia coli* for conversion of glucose to p-hydroxystyrene., Metabolic Engineering, 2007, 9(3):268-276.
Verhoef et al., Bioproduction of p-Hydroxystyrene from Glucose by the Solvent-Tolerant Bacterium Pseudomonas putida S12 in a Two-Phase Water-Decanol Fermentation., Applied and Environmental Microbiology, Feb. 2009, 75(4):931-936.
Verhoef et al., Bioproduction of p-hydroxybenzoate from renewable feedstock by solvent-tolerant *Pseudomonas putida* S12., Journal of Biotechnology, 2007, 132(1):49-56.
Wierckx et al., Engineering of Solvent-Tolerant Pseudomonas putida S12 for Bioproduction of Phenol from Glucose., Applied and Environmental Microbiology, Dec. 2005, 71(12):8221-8227.

(Continued)

*Primary Examiner* — Maryam Monshipouri
(74) *Attorney, Agent, or Firm* — Gavin J. Milczarek-Desai; Quarles & Brady LLP

(57) ABSTRACT

Novel methods for the in vivo production of phenol from renewable substrates using a recombinant microorganism (FIG. 1). Additionally, methods for the in vivo production of catechol and cis,cis-muconic acid from renewable substrates using a recombinant microorganism are disclosed. A host cell expresses at least one gene encoding a polypeptide that possesses isochorismate synthase activity, at least one gene encoding a polypeptide that possesses isochorismate pyruvate lyase activity, and at least one gene encoding a polypeptide that possesses salicylic acid decarboxylase activity. In the case of catechol, the host cell must additionally express at least one gene encoding a polypeptide that possesses phenol 2-monooxygenase activity. In the case of cis,cis-muconic acid, the host cell must additionally express at least one gene encoding a polypeptide that possesses phenol 2-monooxygenase activity and at least one gene encoding a polypeptide that possesses catechol-1,2-dioxygenase activity.

19 Claims, 3 Drawing Sheets
Specification includes a Sequence Listing.

(56) References Cited

OTHER PUBLICATIONS

Dahm et al., The role of isochorismate hydroxymutase genes entC and menF in enterobactin and menaquinone biosynthesis in *Escherichia coli.*, BBA—General Subjects, 1998, 1425(2):377-386.

Serino et al., Structural genes for salicylate biosynthesis from chorismate in Pseudomonas aeruginosa., Mgg Molecular & General Genetics, Mar. 1995, 249(2):217-228.

Van Tegelan et al., Purification and cDNA Cloning of Isochorismate Synthase from Elicited Cell Cultures of Catharanthus roseus., Plant Physiology, Feb. 1999, 119(2):705-712.

Wildermuth et al., Isochorismate synthase is required to synthesize salicylic acid for plant defence., Nature, Nov. 2001, 414(6863):562-565.

Kerbarh et al., Salicylate Biosynthesis: Overexpression, Purification, and Characterization of Irp9, a Bifunctional Salicylate Synthase from Yersinia enterocolitica., Journal of Bacteriology, Aug. 2005, 187(15):5061-5066.

Iwasaki et al., Novel metabolic pathway for salicylate biodegradation via phenol in yeast *Trichosporon moniliiforme.*, Biodegradation, Jul. 2010, 21(4):557-564.

Neujahr et al., Phenol hydroxylase from yeast. Purification and properties of the enzyme from Trichosporon cutaneum., European Journal of Biochemistry, 1973, 35(2):386-400.

Nordlund et al., Complete nucleotide sequence and polypeptide analysis of multicomponent phenol hydroxylase from *Pseudomonas* sp. strain CF600., Journal of Bacteriology, Dec. 1990, 172(12):6826-6833.

Camara et al., A Gene Cluster Involved in Degradation of Substituted Salicylates via ortho Cleavage in *Pseudomonas* sp. Strain MT1 Encodes Enzymes Specifically Adapted for Transformation of 4-Methylcatechol and 3-Methylmuconate., Journal of Bacteriology, Mar. 2007, 189(5):1664-1674.

Nagi et al., Catechol and chlorocatechol 1,2-Dioxygenases., Methods in Enzymology, 1990, 188:122-126.

Nikodem et al., New Bacterial Pathway for 4- and 5-Chlorosalicylate Degradation via 4-Chlorocatechol and Maleylacetate in *Pseudomonas* sp. Strain MT1., Journal of Bacteriology, Dec. 2003, 185(23):6790-6800.

Ikeda et al., Metabolic Engineering to Produce Tyrosine or Phenylalanine in a Tryptophan-Producing *Corynebacterium glutamicum* Strain., Applied and Environmental Microbiology, Mar. 1992, 58(3):781-785.

Krab-Husken, Production of catechols: microbiology and technology., Thesis for Wageningen University, Aug. 2002. 144 pages.

Balderas-Hernandez et al., Catechol biosynthesis from glucose in *Escherichia coli* anthranilate-overproducer strains by heterologous expression of anthranilate 1,2-dioxygenase from Pseudomonas aeruginosa PAO1., Microbial Cell Factories, Oct. 2014, 13:136(11 pages).

Zhang et al., Synthetic biology applications in industrial microbiology., Frontiers in Microbiology, 2014, 5:article 451 (2 pages).

\* cited by examiner

MICROORGANISMS ENGINEERED TO PRODUCE PHENOL AND ITS DERIVATIVES

CROSS-REFERENCE

This application is a 371 application of PCT/US2014/050756 filed Aug. 12, 2014, which claims priority to U.S. provisional patent application 61/870,663 filed on Aug. 27, 2013, which are incorporated by reference herein in their entirety.

FIELD OF THE INVENTION

This disclosure relates to the fields of molecular biology, microbiology, and biotechnology. More specifically, the present disclosure relates to methods of producing phenol, catechol, and cis,cis-muconic acid from simple renewable substrates, such as glucose, in recombinant microorganisms.

BACKGROUND OF THE INVENTION

Phenol is a useful and versatile chemical used for the production of numerous fine and commodity chemicals. Major products of note include bisphenol A (BPA), caprolactam and salicylic acid. For example, in 2007, BPA production accounted for 44% of global phenol consumption and demand. Phenol is also commonly used in the production of numerous polymers, specifically phenolic resins, polycarbonate, and polyamides. Global phenol demand has increased steadily in the last decade. For instance, global phenol demand, which was 6 million tons in 2000, rose to nearly 8 million tons by 2010. Growth has been strongest in the Asia-Pacific region, which is expected to account for >50% of global phenol demand by 2020, by which point is expected to surpass 11.5 million tons. Phenol is typically derived from petrochemical feedstocks including benzene, toluene, and propylene, and as such its market price is tightly correlated with that of crude oil. Presently, an inexpensive and sustainable source of phenol has not yet been developed.

SUMMARY OF THE INVENTION

The embodiments disclosed herein include an in vivo method for the production of phenol via a recombinant host cell co-expressing at least one gene encoding a polypeptide having isochorismate synthase (ICS) activity to convert endogenous chorismate to isochorismate, at least one gene encoding a polypeptide having isochorismate pyruvate lyase (IPL) activity to then subsequently convert isochorismate to salicylates, and at least one gene encoding a polypeptide having salicylate decarboxylase (SDC) activity to convert salicylate to phenol.

The embodiments disclosed herein also include an in vivo method for the production of catechol by further engineering said recombinant host cell to co-express at least one gene encoding a polypeptide that displays phenol 2-monooxygenase (PMO) activity. Further embodiments involve an in vivo method for the production of cis,cis-muconate by further engineering said recombinant host cell to co-express at least one gene encoding a polypeptide that displays catechol-1,2-dioxygenase (CDO) activity. The reaction schemes are illustrated in FIG. 1. These embodiments provide an inexpensive and sustainable biological route for the conversion of renewable substrates to phenol, catechol, and cis,cis-muconate. All three products are useful, for example, for the synthesis of numerous chemical and polymer products.

These and other aspects of the invention will be apparent upon reference to the following detailed description and figures. To that end, any patent and other documents cited herein are hereby incorporated by reference in their entirety.

DETAILED DESCRIPTION OF THE PREFERRED EMBODIMENTS

Figure 1:
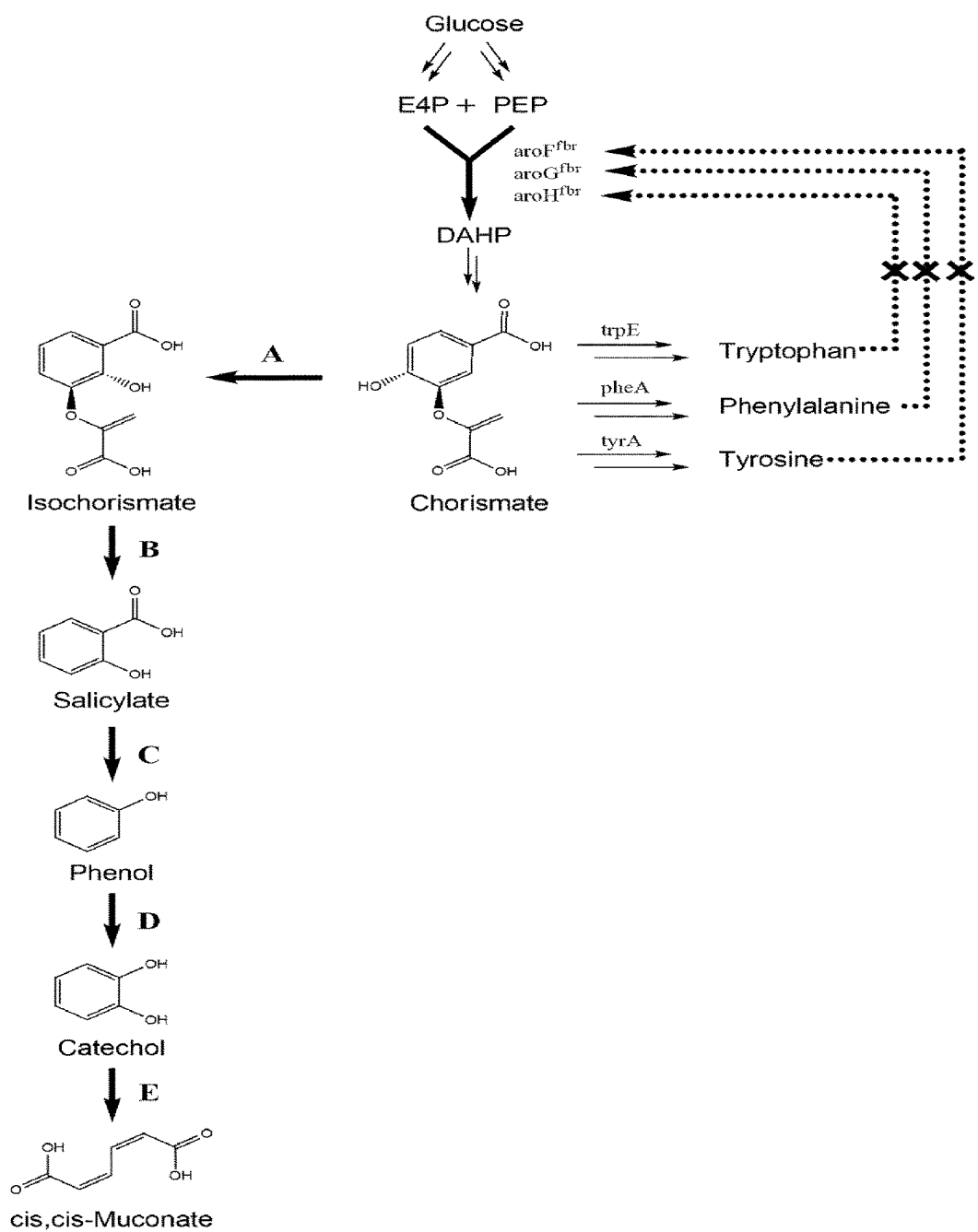
FIG. 1 depicts an enzymatic pathway to convert the endogenous precursor chorismate to the product phenol via the intermediates isochorismate and salicylate. The three-step pathway from chorismate is achieved by the co-expression of one or more genes encoding polypeptides with the following activities: isochorismate synthase (ICS; A), isochorismate pyruvate lyase (IPL; B), and salicylate decarboxylase (SDC; C). The additional co-expression of one or more genes encoding phenol 2-monooxygnease (PMO; D) results in the production of catechol. The additional co-expression of one or more genes encoding catechol-1,2-dioxygenase (CDO; E) results in the production of cis,cis-muconate.

The following abbreviations and definitions will be used for the interpretation and specification of the claims:

"isochorismate synthase" is abbreviated ICS.
"isochorismate pyruvate lyase" is abbreviated IPL.
"salicylate decarboxylase" is abbreviated SDC.
"phenol 2-monooxygenase" is abbreviated PMO.
"catechol-1,2-dioxygenase" is abbreviated CDO.

As used herein, the terms "L-phenylalanine", and "phenylalanine" are used interchangeably.

As used herein, the terms "cis,cis-muconic acid", "muconic acid", cis,cis-muconate", and "muconate" are used interchangeably.

As used herein, the terms "chorismic acid" and "chorismate" are used interchangeably.

As used herein, the terms "isochorismic acid" and "isochorismate" are used interchangeably.

As used herein, the terms "salicylic acid" and "salicylate" are used interchangeably.

As used herein, the terms "pyruvic acid" and "pyruvate" are used interchangeably.

As used herein, the terms "phenol 2-monoxygenase", and "phenol hydroxylase" are used interchangeably.

The term "ICS activity" refers to the ability of a protein to catalyze the direct conversion of chorismate to isochorismate.

The term "IPL activity" refers to the ability of a protein to catalyze the direct conversion of isochorismate to salicylate.

The term "SDC activity" refers to the ability of a protein to catalyze the direct conversion of salicylate to phenol.

The term "PMO activity" refers to the ability of a protein to catalyze the direct conversion of phenol to catechol.

The term "CDO activity" refers to the ability of a protein to catalyze the direct conversion of catechol to cis,cis-muconate.

The term "chorismate over-producing strain" refers to a microbial strain that produces endogenous levels of chorismate that are significantly higher than those demonstrated by the wild-type of that strain. Specific examples of an *E. coli* chorismate over-producing strains are NST74 and NST37 (U.S. Pat. No. 4,681,852). Meanwhile, still others may include specific strains of *Corynebacterium glutamicum*[16].

The term "fermentable carbon substrate" refers to a carbon source capable of being metabolized by the host organisms of the present invention and particularly carbon sources selected from the group consisting of monosaccharides, oligosaccharides, polysaccharides, organic acids, glycerol, and one-carbon substrates or mixtures thereof.

The term "host" refers to a suitable cell line such as a strain of bacteria, for example, into which genes can be transferred to impart desired genetic attributes and functions.

The term "$OD_{600}$" refers to the measurement of optical density at 600 nm, a standard metric of cell growth used by those familiar in the art.

The term "gene" refers to a nucleic acid fragment that expresses a specific protein, including regulatory sequences preceding (5' non-coding sequences) and following (3' non-coding sequences) and the coding sequence. "Native gene" or "wild type gene" refers to a gene as found in nature with its own regulatory sequences. "Endogenous gene" refers to a native gene in its natural location in the genome of an organism. "Foreign gene" refers to a gene not normally found in the host organism but that is introduced into the host organism by gene transfer. Foreign genes can comprise native genes inserted into a non-native organism, or chimeric genes.

The term "expression", as used herein, refers to the transcription and stable accumulation of sense (mRNA) or antisense RNA derived from the nucleic acid fragment used in this invention. Expression may also refer to the translation of the mRNA into a polypeptide. "Overexpression" refers to the production of a gene product in a transgenic organism that exceeds levels of production in the wild-type host or native organisms.

"RNA transcript" refers to the product resulting from RNA polymerase-catalyzed transcription of gene or other a DNA sequence. "Messenger RNA (mRNA)" refers to the RNA that is without introns and can be translated into a protein by the cell. "cDNA" refers to double-stranded DNA that is complimentary to and derived from mRNA. "Sense" RNA refers to RNA transcript that includes the mRNA and so can be translated into protein by the cell.

"Transformation" refers to the transfer of a nucleic acid fragment into the genome genome of the host organism, resulting in genetically-stable inheritance. Host organisms containing the transformed nucleic acid fragments are referred to as "transgenic" or "recombinant" or "transformed" organisms.

The terms "plasmid" and "vector" refer to an extra chromosomal genetic element often carrying genes which are not part of host native genome nor the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

It would be an advancement in the current state of the art to provide a method by which phenol could be produced from inexpensive and sustainable resources such as carbohydrates or sugars. It would be particularly advantageous if the method produced a high level of phenol at high substrate yields and with a limited diversity and quantity of by-products. The development of such a method requires the ability to manipulate and assemble the appropriate genetic machinery responsible for the conversion of carbohydrates, such as glucose, to chorismate, chorismate to isochorismate, isochorismate to salicylate, and salicylate to phenol. It would be exceptionally advantageous if these conversions could all be achieved within a single host cell.

Efficient biological production of phenol is difficult. Therefore, the problem to be overcome is to design and develop a method for the efficient production of phenol by a biological source using inexpensive substrates as the carbon source. The applicants have solved the stated problem by engineering a microbial host to produce phenol by expression of foreign genes encoding each of isochorismate synthase (ICS), isochorismate pyruvate lyase (IPL), and salicylate decarboxylase (SDC).

Furthermore, catechol may be produced by the enzymatic oxidation of phenol by the additional co-expression of one or more genes encoding a polypeptide with phenol 2-monooxygenase (PMO) activity. Further, cis,cis-muconate may be produced by the enzymatic ring-opening oxidation of catechol by the additional co-expression of one or more genes encoding a polypeptide with catechol-1,2-dioxygenase (CDO) activity. cis,cis-Muconate is a platform molecule useful for the synthesis of many plastics precursors.

Genes

The key enzymatic activities used in the present embodiments are encoded by a number of genes known in the art. The principal enzyme activities include isochorismate synthase (ICS), isochorismate pyruvate lyase (IPL), salicylate decarboxylase (SDC), phenol 2-monooxygenase (PMO), and catechol-1,2-dioxygenase (CDO). These activities may also be displayed by enzymes whose principal natural substrates are not chorismate, isochorismate, salicylate, phenol, or catechol respectively, but also those which have the natural capacity to utilize these substrates or which can be engineered to display these activities.

Isochorismate Synthase (ICS), Isochorismate Pyruvate Lyase (IPL), Salicylate Decarboxylase (SDC), Phenol 2-Monooxygenase (PMO), and Catechol-1,2-Dioxygenase (CDO) Activities Genes encoding ICS activity are known in the art and several have been sequenced from both microbial and plant origin. The sequence of ICS encoding genes are available (for example, see GenBank Gene ID: 945511, 946712, 881821, and 843810). Genes encoding IPL activity are known in the art and several have been sequenced from microbial origin. The sequence of IPL encoding genes are available (for example, see GenBank Gene ID: 881846). Genes encoding SDC activity are known in the art and to date only one has been sequenced from microbial origin. The sequence of SDC encoding genes are available (for example, see DDBJ ID: DM040453). Genes encoding PMO activity are known in the art and have been sequenced. The sequence of PMO encoding genes are available (for example, see GenBank Accession: L04488.1 and M60276.1). Genes encoding CDO activity are known in the art and have been sequenced. The sequence of CDO encoding genes are available (for example, see GenBank Gene ID: 3609645, 3614680, 879147, 5191661, and 5191980).

It will be appreciated that the present embodiments are not limited to the genes encoding polypeptides having the specific activities mentioned above, but will encompass any suitable homologs of such genes that may be obtained by standard methods. Methods of obtaining homologs to these genes using sequence-dependent protocols are well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR)).

For example, genes encoding homologs of the polypeptides that alone or in combination have the above mentioned activities could be isolated directly by using all or a portion of the known sequences as DNA hybridization probes to screen libraries from any desired plant, fungi, yeast, or bacteria using methodology well known to those skilled in the art. Specific oligonucleotide probes based upon the literature nucleic acid sequences can be designed and synthesized by methods known in the art. Moreover, the entire sequences can be used directly to synthesize DNA probes by methods known to those skilled in the art, such as random primers DNA labeling, nick translation, or end-labeling techniques or RNA probes using available in vitro transcription systems. In addition, specific primers can be designed and used to amplify a part of or full length of the instant sequences. The resulting amplification products can be labeled directly during amplification reactions or labeled after amplification reactions, and used as probes to isolate full-length cDNA or genomic fragments under conditions of appropriate stringency.

Microbial Production Hosts

The production organisms of the present invention will include any organism capable of expressing the genes required for phenol production. Typically, the production organism will be restricted to microorganisms or plants. Microorganisms useful in the present invention include, but are not limited to enteric bacteria (*Escherichia* and *Salmonella*, for example) as well as *Bacillus, Acinetobacter, Actinomycetes* such as *Streptomyces, Corynebacterium, Methanotrophs* such as *Methylosinus, Methylomonas, Rhodococcus* and *Pseudomonas; Cyanobacteria*, such as *Rhodobacter* and *Synechocystis*; yeasts, such as *Saccharomyces, Zygosaccharomyces, Kluyveromyces, Candida, Hansenula, Debaryomyces, Mucor, Pichia,* and *Torulopsis*; and filamentous fungi such as *Aspergillus* and *Arthrobotrys*, and algae, for example. Co-expressing at least one gene encoding a polypeptide having ICS activity, at least one gene encoding a polypeptide having IPL activity, and at least one gene encoding a polypeptide having SDC activity can result in the production of large quantities of phenol.

Although any of the above mentioned microorganisms would be useful for the production of phenol, preferred strains would be those that either natively or have been engineered to over-produce chorismate. Chorismate over-producing strains are known and include, but are not limited to, *Escherichia* sp., *Corynebacterium* sp., *Microbacterium* sp., *Arthrobacter* sp., *Pseudomonas* sp., and *Brevibacteria* sp. Particularly useful chorismate over-producing strains include, but are not limited to, *Microbacterium ammoniaphilum* ATCC 10155, *Corynebacterium lillium* NRRL-B-2243, *Corynebacterium glutamicum* ATCC 21674, *E. coli* NST74, *E. coli* NST37, and *Arthrobacter citreus* ATCC 11624.

A recombinant host for phenol production may be constructed from a suitable chorismate over-producing strain by co-expressing at least one gene encoding a polypeptide having ICS activity, at least one gene encoding a polypeptide having IPL activity, and at least one gene encoding a polypeptide having SDC activity.

Microbial expression systems and expression vectors containing regulatory sequences that direct high level expression of foreign proteins and over-expression of native proteins are well known to those skilled in the art. Any of these could be used to construct chimeric genes for the production of phenol, as well as its derivatives catechol and cis,cis-muconic acid. These chimeric genes could then be introduced into appropriate microorganisms via transformation to allow for expression of high levels of the enzymes.

The method of production associated with embodiments of the invention involves the incorporation of genes encoding polypeptides displaying ICS, IPL, SDC, PMO, and CDO activities into a single host organism and the use of those organisms to convert renewable resources such as glucose, for example, to phenol and its derivatives, catechol and cis-cis-muconate. Thus, embodiments of the invention rely upon the identification of genes encoding ICS, IPL, SDC, PMO, and CDO activities and, preferably, those genes which when expressed in a recombinant host organism can display such activities. Candidate genes encoding ICS homologs were selected and included ICS1 from *Arabidopsis thaliana*, pchA from *Pseudomonas aeruginosa*, entC from *E. coli*, and menF from *E. coli*. Each gene was amplified from genomic DNA samples via PCR, cloned into an appropriate expression vector, and transformed into *E. coli*. Candidate genes encoding IPL were selected from the open literature and included pchB from *Pseudomonas aeruginosa*. Each gene was amplified from genomic DNA samples via PCR, cloned into an appropriate expression vector, and transformed into *E. coli*. Candidate genes encoding SDC were selected from the open literature and included sdc from *Trichosporon moniliiforme*. The gene was synthesized to include codon optimization for *E. coli*, then subsequently amplified via PCR, cloned into an appropriate expression vector, and transformed into *E. coli*. Candidate genes encoding PMO were selected and included the operon dmpLMNOP from *Pseudomonas* sp. CF600 and loci GI:170525 from *Trichosporon cutaneum*. Candidate genes encoding CDO were selected and included catA from *Pseudomonas reinekei*, salD from *Pseudomonas reinekei*, and catA from *Pseudomonas putida*.

Where possible, screening assays were then performed on both whole cells and cell extracts. SDC activity was investigated via the conversion of exogenous salicylate to phenol, whereas PMO activity was investigated via the conversion of exogenous phenol to catechol, and CDO activity was investigated via the conversion of exogenous catechol to cis,cis-muconic acid. SDC activity was positively confirmed in recombinant *E. coli* according to both whole cell and cell extract assays in strains expressing codon optimized sdc synthesized based on the wild-type sequence of *Trichosporon moniliiforme*.

EXAMPLES

It should be understood that these Examples, while indicating preferred embodiments of the invention, are given by way of illustration only. From the above discussion and these following Examples, one skilled in the art can ascertain the essential characteristics of this invention, and without departing from the spirit and scope thereof, can make various changes and modifications of the invention to adapt it to various uses and conditions.

Procedures required for PCR amplification, DNA modifications by endo- and exonucleases for generating desired ends for cloning of DNA, ligation, and bacterial transformation are well known in the art. The standard molecular biology techniques used herein are well-known in the art and described by Sambook, J., Fritsch, E. F., and Maniatis, T., *Molecular Cloning: A Laboratory Manual*, $2^{nd}$ ed.; Cold Spring Harbor Laboratory: Cold Spring Harbor, N.Y., 1989.

Materials and methods suitable for the maintenance and growth of microbial cultures are well known in the art. Method and techniques suitable for use in the following set of Examples may be found for example, as described in Manual of Methods for General Bacteriology; Gerhardt, P., Murray, R. G. F., Costilow, R. N., Nester, E. W., Wood, W. A., Krieg, N. R., and Phillips, G. B., Eds., American Society for Microbiology: Washington, D.C., 1994. All reagents used in the Examples were purchased from Sigma Aldrich (St. Louis, Mo.). Restriction enzymes, polymerases, and ligase were purchased from New England Biolabs (Ipswich, Mass.). Nutrients and chemicals used for the growth and maintenance of cells were purchased from DIFCO Laboratories (Detroit, Mich.).

General Methods

PCR reactions were performed using a BioRad iCycler system with Phusion DNA Polymerase (Finnzymes, Espoo, Finland). Custom DNA oligonucleotide primers were synthesized by and purchased from Integrated DNA Technologies (Coralville, Iowa). PCR cycling and reaction conditions were standardized according to manufacturer instructions.

An HPLC assay was developed to simultaneously separate and measure aqueous metabolite concentrations in microbial cultures. For a typical assay, 1 mL culture was removed from shake flask culture and centrifuged to pellet cells. 0.75 mL of supernatant was then transferred to a sealed HPLC vial. A Hewlett Packard 1100 series HPLC system with an auto sampler and a diode array UV/Vis detector with a reverse-phase Hypersil Gold SBC18 column (4.6 mm×150 mm; Thermo Fisher, USA) was used to achieve separation and detection of the species. 5 was used to achieve separation and detection of the species. nd a diode arrayA total flow rate of 1.0 ml/min and column temperature of 45° C. were held constant throughout. The column was eluted with solvent A containing 5 mM sulfuric acid and solvent B containing acetonitrile. The eluent consists of 85% solvent A and 15% solvent B. The UV detector was used to monitor the eluent at 215 nm for phenol and salicylate. Under these conditions phenol and salicylate were eluted at 6.8 min and 12.6 min, respectively.

For all culture experiments, seeds cultures were first grown in Luria Broth (LB) media overnight. Minimal media 1 (herein referred to as "MM1") was used for fermentations which contained glucose (nominally 15 g/L), $MgSO_4.7H_2O$ (0.5 g/L), $NH_4SO_4$ (4.0 g/L), MOPS (24.7 g/L), $KH_2PO_4$ (0.3 g/L), $K_2HPO_4$ (0.7 g/L), and 5 mL/L ATCC Trace Mineral Supplement (EDTA(0.5 g/L), $MgSO_4.7H2O$ (3 g/L), $MnSO_4.7H_2O$ (0.5 g/L), NaCl (1 g/L), $FeSO_4.7H_2O$ (0.1 g/L), $Co(NO_3)_2.6H_2O$ (0.1 g/L), $CaCl_2$ (0.1 g/L), $ZnSO4.7H_2O$ (0.1 g/L), $CuSO_4.5H_2O$ (0.01 g/L), $AlK(SO_4)_2$ (0.01 g/L), $H_3BO_3$ (0.01 g/L), $Na_2MoO_4.2H_2O$ (0.01 g/L), $Na_2SeO_3$ (0.001 g/L), $Na_2WO_4.2H_2O$ (0.10 g/L), and $NiCl_2.6H_2O$ (0.02 g/L)).

Cloning of Candidate Genes Encoding ICS Activity from *E. Coli, A. Thaliana*, and *P. Aeruginosa*.

Candidate ICS encoding genes, namely SEQ ID NO:1, SEQ ID NO:2, SEQ ID NO:3, and SEQ ID NO:4 were amplified via PCR using clonal and genomic DNA templates derived from *A. thaliana* (SEQ ID NO:1), *P. aeruginosa* (SEQ ID NO:2), and *E. coli* (SEQ ID NO:3 and SEQ ID NO:4). The oligonucleotide primers used to amplify IcsI from *A. thaliana* (SEQ ID NO:1) are given as SEQ ID NO:8 and SEQ ID NO:9. The oligonucleotide primers used to amplify pchA from *P. aeruginosa* (SEQ ID NO:2) are given as SEQ ID NO:10 and SEQ ID NO:11. The oligonucleotide primers used to amplify menF from *E. coli* (SEQ ID NO:3) are given as SEQ ID NO:12 and SEQ ID NO:13. The oligonucleotide primers used to amplify entC from *E. coli* (SEQ ID NO:4) are given as SEQ ID NO:14 and SEQ ID NO:15. In all cases, amplified linear DNA fragments were subsequently cleaned using Zyppy Clean and Concentrator kit (Zymo Research, Orange, Calif.). Amplified fragments from *A. thaliana, P. aeruginosa* and *E. coli* were then treated by restriction endonuclease digestion with the enzymes BamHI and XbaI with appropriate digestion buffer for 3 h at 37° C. Samples of the expression vector pTrc99A were similarly digested with BamHI and XbaI. All digested fragments were subsequently purified using the Zyppy Gel DNA recovery kit (Zymo Research, Orange, Calif.) per manufacturer's instruction. Gene inserts and linearized plasmid DNA were then appropriately ligated together by treatment with T4 DNA ligase (New England Biolabs, Ipswich, Mass.) at 4° C. overnight. Ligase reaction mixtures were then transformed into chemically competent *E. coli* NEB10-Beta. Selection of transformants was achieved by plating transformed cells on LB solid agar media containing 100 mg/L ampicillin and culturing overnight at 37° C. Vectors with correct gene insert for all ICS encoding genes were confirmed by restriction digest analysis and colony PCR with 1 µL culture broth and appropriate primers, namely SEQ ID NO:8, SEQ ID NO:9, SEQ ID NO:10, SEQ ID NO:11, SEQ ID NO:12, SEQ ID NO:13, SEQ ID NO:14, and SEQ ID NO:15. Under these conditions, vectors containing the correct gene insert were identified as those which displayed fragments of 1.7 kb (IcsI), 1.4 kb (pchA), 1.3 kb (menF), and 1.2 kb (entC) when separated on a 0.7% w./v. agarose gel at 90V for 60 min. These cloning works resulted in the successful generation of the plasmids pTrc99A-IcsI, pTrc99A-pchA, pTrc99A-menF, and pTrc99A-entC.

Cloning of Candidate Genes Encoding IPL Activity from *P. aeruginosa*.

Candidate IPL encoding genes, namely SEQ ID NO:5, was amplified via PCR using genomic DNA templates derived from *P. aeruginosa*. The oligonucleotide primers used to amplify pchB from *P. aeruginosa* (SEQ ID NO:5) are given as SEQ ID NO:16 and SEQ ID NO:17. Amplified DNA fragments were subsequently cleaned using Zyppy Clean and Concentrator kit (Zymo Research, Orange, Calif.). Fragments were then treated by restriction enzyme digestion with appropriate enzymes and buffer for 3 h at 37° C. Amplified fragments of pchB were digested with NcoI and EcoRI for which the previously engineered vectors pTrc99A-IcsI, pTrc99A-pchA, pTrc99A-menF, and pTrc99A-entC were also digested with NcoI and EcoRI. All digested fragments were subsequently purified using the Zyppy Gel DNA recovery kit (Zymo Research, Orange, Calif.) per manufacturers instruction. Gene inserts and linearized plasmid DNA were then appropriately ligated together by treatment with T4 DNA ligase (New England Biolabs, Ipswich, Mass.) at 4° C. overnight.

Ligase reaction mixtures were then transformed into chemically competent *E. coli* NEB10-Beta. Selection of transformants was achieved by plating transformed cells on LB solid agar media containing 100 mg/L ampicillin and culturing overnight at 37° C. Among the resultant transformants, the vectors with the correct insertion of the genes IcsI/pchB, pchA/pchB, menF/pchB, and entC/pchB were confirmed among clones by restriction digest analysis and colony PCR with 1 µL culture broth and appropriate primers, namely SEQ ID NO:8, SEQ ID NO:9, SEQ ID NO:10, SEQ ID NO:11, SEQ ID NO:12, SEQ ID NO:13, SEQ ID NO:14, SEQ ID NO:16, and SEQ ID NO:17. Under these conditions, vectors containing the correct gene inserts were identified as those which displayed fragments of 1.7 kb (IcsI), 1.4 kb (pchA), 1.3 kb (menF), 1.2 kb (entC), and 0.3 kb (pchB) when separated on a 0.7% w./v. agarose gel at 90V for 60 min. These cloning works resulted in the successful generation of the plasmids pTrc99A-IcsI-pchB, pTrc99A-pchA-pchB, pTrc99A-menF-pchB, and pTrc99A-entC-pchB.

Cloning of Candidate Genes Encoding SDC Activity.

The candidate salicylate decarboxylase encoding gene, sdc_syn (SEQ ID NO:7), was amplified via PCR using a template plasmid containing a synthetic gene sequence custom synthesized for codon optimization in *E. coli* and based on the wild-type sequence of sdc from *T. moniliiforme* (SEQ ID NO:6). The oligonucleotides primers used to amplify sdc_syn (SEQ ID NO:7) are given as SEQ ID NO:18 and SEQ ID NO:19. Amplified DNA fragments were subsequently cleaned using Zyppy Clean and Concentrator kit (Zymo Research, Orange, Calif.). Amplified fragments were then treated by restriction endonuclease digestion with the enzymes NcoI and EcoRI with appropriate digestion buffer for 3 h at 37° C. A sample of the expression vector pTrcCOLAK was similarly digested with NcoI and EcoRI. Digested fragments were subsequently cleaned using Zyppy Gel DNA recovery kit (Zymo Research, Orange, Calif.). Gene inserts and linearized plasmid DNA were ligated together by treatment with T4 DNA ligase (New England Biolabs, Ipswich, Mass.) at 4° C. overnight. Ligation mixtures were subsequently transformed into chemically competent *E. coli* NEB10-beta (New England Biolabs, Ipswich, Mass.). Selection of transformants was achieved by plating transformed cells on LB solid agar media containing 35 mg/L kanamycin and culturing overnight at 37° C. Vectors with correct gene insert for all SDC encoding genes were confirmed by restriction digest analysis and colony PCR with 1 µL culture broth and appropriate primers, namely SEQ ID NO:18 and SEQ ID NO:19. Under these conditions, vectors containing the correct gene insert were identified as those which displayed a fragment of 1.0 kb (sdc) when separated on a 0.7% w./v. agarose gel at 90V for 60 min. This cloning effort resulted in the successful generation of the plasmid pTrcCOLAK-sdc_syn.

Example 1

Assaying SDC Activity in Recombinant *E. Coli*.

Figure 2:
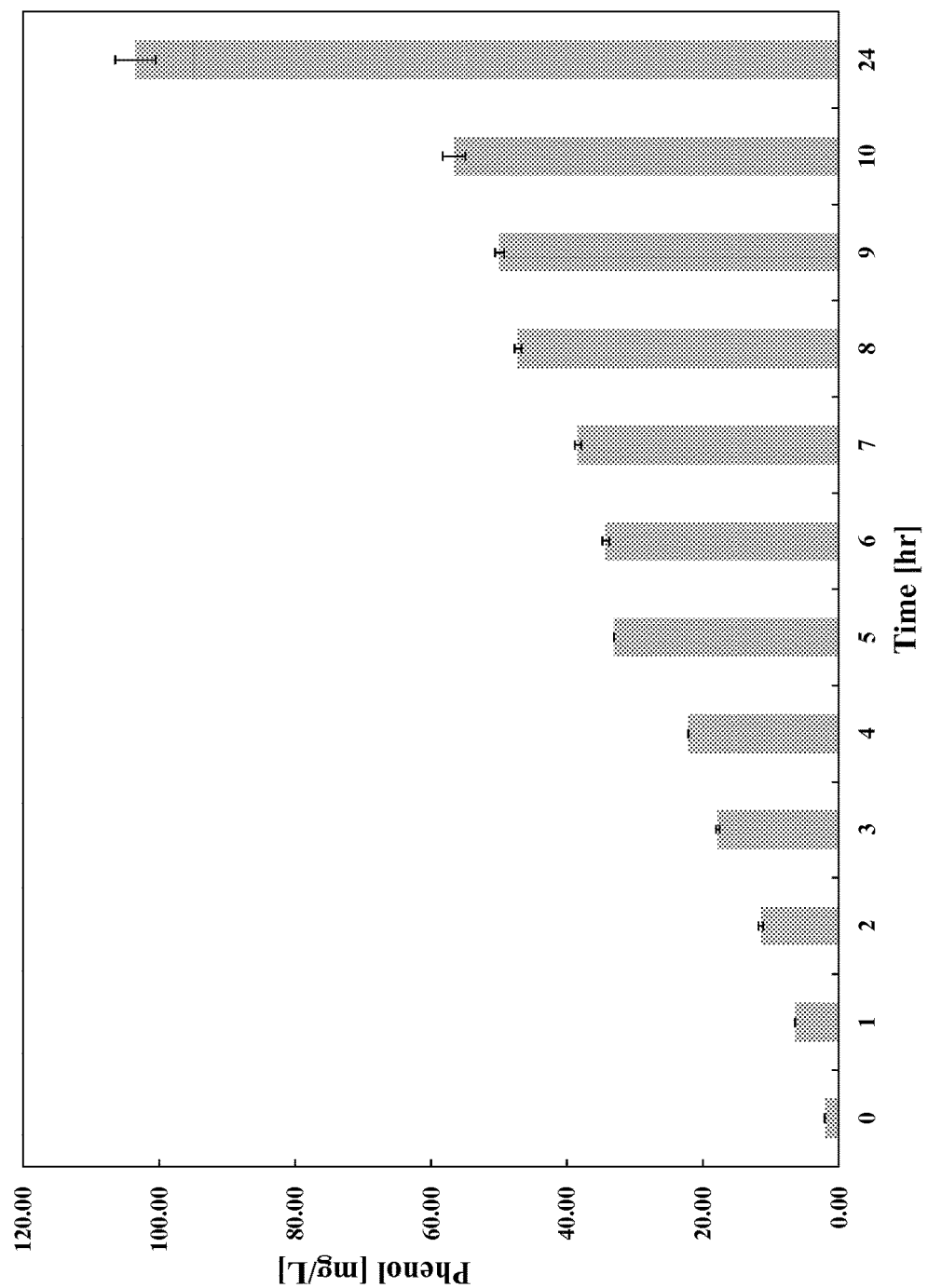
FIG. 2 depicts phenol production from salicylate by E. coli BW25113(DE3) pTrcCOLAK-sdc_syn. 50 ml cultures were grown for overnight (induced with 0.2 mM IPTG after 6 hours), pelleted, and then resuspended in 10 ml PBS buffer supplemented with 400 mg/L salicylate. Phenol accumulation in the extracellular medium over a 24 hour period is shown.

SDC activity was investigated using a whole cell assay. *E. coli* BW25113(DE3) was first transformed with pTrcCO-LAK-sdc_syn. Selection was performed on LB agar supplemented with 35 mg/L kanamycin and screened for said resistance. This resulted in the construction of the strain *E. coli* BW25113(DE3) pTrcCOLAK-sdc_syn. Two seed cultures of *E. coli* BW25113(DE3) pTrcCOLAK-sdc_syn consisting of 5 ml of LB broth containing 100 mg/L ampicillin and 35 mg/L kanamycin were prepared and grown overnight at 37° C. while shaking at 200 rpm. 1 mL of each culture was used to inoculate 3×250 mL shake flasks containing 50 mL of LB supplemented with 100 mg/L ampicillin and 35 mg/L kanamycin. Cultures were grown at 30° C. while shaking at 200 rpm for 6 h at 30° C. before being induced with IPTG to a final concentration of 0.2 mM. Induced cultures were then allowed to grow overnight at 30° C. while shaking at 200 rpm. Cells were then collected by centrifugation in 50 ml Falcon tubes for 5 min at 1400×g and washed once with PBS (phosphate buffered saline, pH 7) buffer. The entire cell pellet was then resuspended in 30 ml PBS supplemented with 400 mg/L salicylate. The results for this assay are shown in FIG. 2, which show that expression of pTrcCO-LAK-sdc_syn in *E. coli* BW25113(DE3) results in the conversion of salicylate to phenol at a final titer greater than 100 mg/L phenol.

These results demonstrate how SDC activity can be attained in recombinant *E. coli* by the expression of a gene whose sequence is given by SEQ ID NO:7. These results further establish the generation of recombinant *E. coli* strains that are specifically capable of converting salicylate to phenol.

Example 2

Co-Expression of ICS, IPL, and SDC Encoding Enzymes in *E. Coli* NST 74 to Convert Glucose to Phenol in Flask Cultures.

Figure 3:
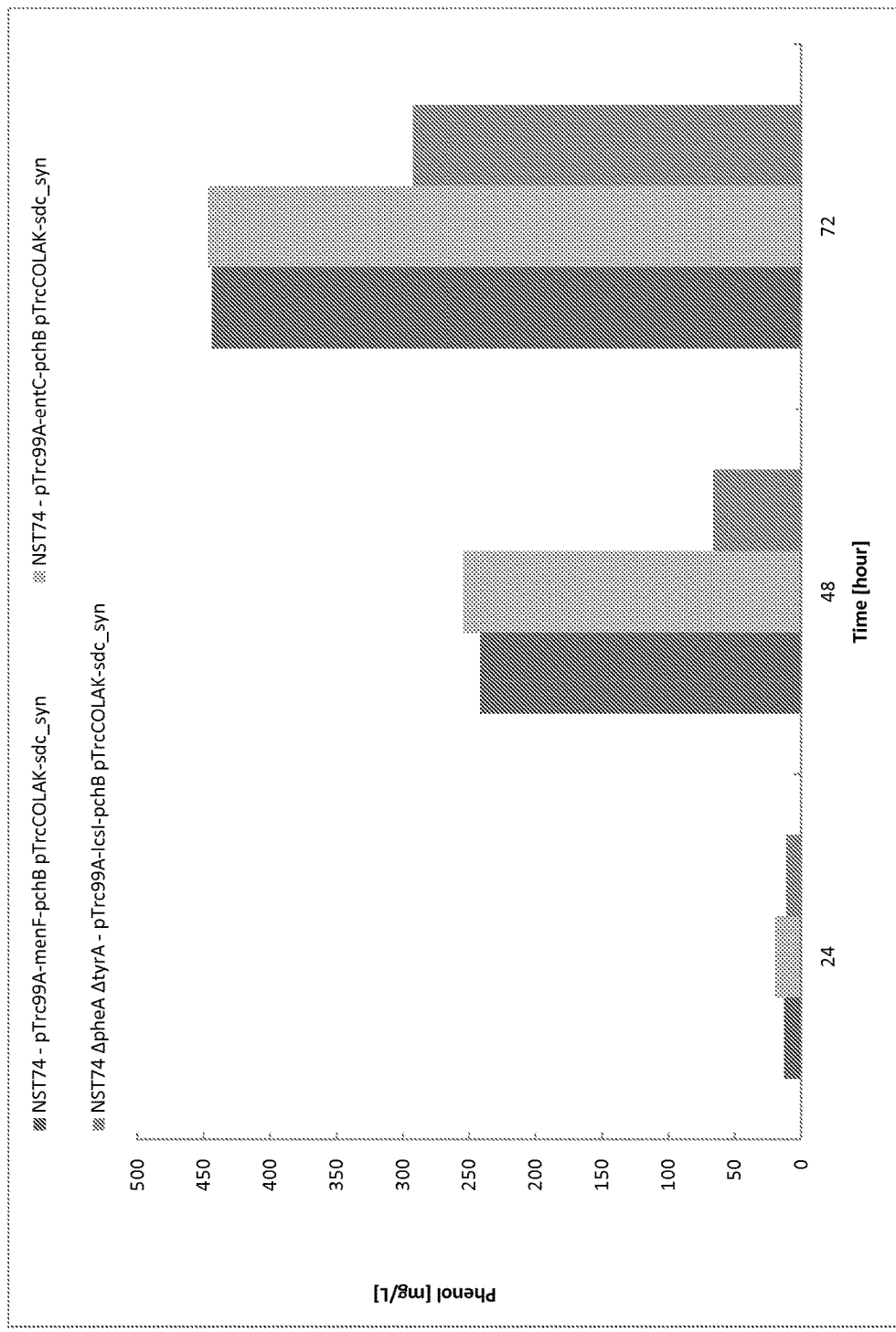
FIG. 3 shows conversion of glucose to phenol in shake flask cultures by (1) E. coli NST74 pTrc99A-menF-pchB pTrcCOLAK-sdc_syn, (2) E. coli NST74 pTrc99A-entC-pchB pTrcCOLAK-sdc_syn and (3) E. coli NST74 ΔpheAΔtyrA pTrc99A-IcsI-pchB pTrcCOLAK-sdc_syn over a 72 hour period.

The previously-engineered phenylalanine over-producing strain *E. coli* NST74 was co-transformed with plasmids pTrc99A-menF-pchB and pTrcCOLAK-sdc_syn, and pTrc99A-entC-pchB and pTrcCOLAK-sdc_syn. The previously-engineered phenylalanine over-producing strain *E. coli* NST74 ΔpheAΔtyrA was co-transformed with plasmids pTrc99A-IcsI-pchB and pTrcCOLAK-sdc_syn. Selection was performed on LB agar supplemented with 100 mg/L ampicillin and 35 mg/L kanamycin and screened for said resistances. This resulted in the construction of the strains (1) *E. coli* NST74 pTrc99A-menF-pchB pTrcCO-LAK-sdc_syn, (2) *E. coli* NST74 pTrc99A-entC-pchB pTrc-COLAK-sdc_syn, and (3) *E. coli* NST74 ΔpheAΔtyrA pTrc99A-IcsI-pchB pTrcCOLAK-sdc_syn. Single colonies were then selected from the resultant transformants and those strains were grown in 5 mL LB broth supplemented with both 100 mg/L ampicillin and 35 mg/L kanamycin. These seed cultures were grown for 12 hours at 32° C. with shaking at 250 rpm. 1 ml of each seed culture was then used to inoculate 50 mL MM1 supplemented with 100 mg/L ampicillin and 35 mg/L kanamycin. These cultures were performed in 250 mL shake flasks. The cells were then grown at 30° C. with shaking at 250 rpm to an $OD_{600}$ ~0.6 prior to being induced by the addition of IPTG to a final concentration of 0.4 mM. 1 ml samples were taken from each culture at intervals of 0, 24, 48, and 72 hours post induction and analyzed for metabolite content via HPLC-DAD using methods described herein. The obtained results are shown in FIG. 3. As can be seen, all three strains are capable of producing phenol from glucose, with *E. coli* NST74 pTrc99A-entC-pchB pTrcCOLAK-sdc_syn in particular producing phenol to a final titer of greater than 440 mg/L after 72 h.

These results illustrate how a strain of *E. coli* can be constructed to synthesize phenol as a dominant product when supplied with glucose as a sole carbon and energy source. The invention describes a process in which recombinant *E. coli* has been engineered to co-express enzymes that display both ICS, IPL and SDC activities. In the preferred embodiments, the *E. coli* host strain will be a chorismate over-producing strain, ICS activity will be encoded by menF or entC from *E. coli*, IPL activity will be encoded by pchB from *P. aeruginosa*, and SDC activity will be encoded by a gene whose sequence is given by (SEQ ID NO:7).

Accordingly, the embodiments described and illustrated above provide a method for the production of phenol comprising:
i) contacting a recombinant host cell with a fermentable carbon source, said recombinant host comprising:
a) at least one gene encoding a polypeptide having isochorismate synthase activity; and
b) at least one gene encoding a polypeptide having isochorismate pyruvate lyase activity; and
c) at least one gene encoding a polypeptide having salicylate decarboxylase activity
ii) growing said recombinant cell for a time sufficient to produce phenol Additionally, the embodiments described and illustrated above provide a method for the production of catechol comprising:
i) contacting a recombinant host cell with a fermentable carbon source, said recombinant host comprising:
a) at least one gene encoding a polypeptide having isochorismate synthase activity; and
b) at least one gene encoding a polypeptide having isochorismate pyruvate lyase activity; and
c) at least one gene encoding a polypeptide having salicylate decarboxylase activity; and
d) at least one gene encoding a polypeptide having phenol 2-monooxygenase activity
ii) growing said recombinant cell for a time sufficient to produce catechol Additionally, the embodiments described and illustrated above provide a method for the production of cis,cis-muconate comprising:
i) contacting a recombinant host cell with a fermentable carbon source, said recombinant host comprising:
a) at least one gene encoding a polypeptide having isochorismate synthase activity; and
b) at least one gene encoding a polypeptide having isochorismate pyruvate lyase activity; and
c) at least one gene encoding a polypeptide having salicylate decarboxylase activity; and
d) at least one gene encoding a polypeptide having phenol 2-monooxygenase activity; and
e) at least one gene encoding a polypeptide having catechol-1,2-dioxygenase activity
ii) growing said recombinant cell for a time sufficient to produce cis,cis-muconate Additionally, the embodiments described and illustrated above provide a recombinant host cell comprising:
a) at least one gene encoding a polypeptide having isochorismate synthase activity; and
b) at least one gene encoding a polypeptide having isochorismate pyruvate lyase activity; and
c) at least one gene encoding a polypeptide having salicylate decarboxylase activity Additionally, the embodiments described and illustrated above provide a recombinant host cell comprising:
a) at least one gene encoding a polypeptide having isochorismate synthase activity; and
b) at least one gene encoding a polypeptide having isochorismate pyruvate lyase activity; and
c) at least one gene encoding a polypeptide having salicylate decarboxylase activity; and
d) at least one gene encoding a polypeptide having phenol 2-monooxygenase activity Additionally, the embodiments described and illustrated above provide a recombinant host cell comprising:
a) at least one gene encoding a polypeptide having isochorismate synthase activity; and
b) at least one gene encoding a polypeptide having isochorismate pyruvate lyase activity; and
c) at least one gene encoding a polypeptide having salicylate decarboxylase activity; and
d) at least one gene encoding a polypeptide having phenol 2-monooxygenase activity; and
e) at least one gene encoding a polypeptide having catechol 1,2-dioxygenase activity The materials and methods described above are not intended to be limited to the embodiments and examples described herein.

What is claimed is:

1. A method for the production of phenol comprising:
   (i) contacting a bacterial or yeast recombinant host cell with a fermentable carbon substrate, said bacterial or yeast recombinant host cell comprising and co-expressing:
   a) at least one gene encoding a polypeptide having isochorismate synthase activity;
   b) at least one gene encoding a polypeptide having isochorismate pyruvate lyase activity; and
   c) at least one gene encoding a polypeptide having salicylate decarboxylase activity; and
      (ii) growing said recombinant cell for a time sufficient to produce phenol.

2. A method for the production of catechol comprising:
   (i) contacting a bacterial or yeast recombinant host cell with a fermentable carbon substrate, said bacterial or yeast recombinant host cell comprising and co-expressing:
   a) at least one gene encoding a polypeptide having isochorismate synthase activity;
   b) at least one gene encoding a polypeptide having isochorismate pyruvate lyase activity;
   c) at least one gene encoding a polypeptide having salicylate decarboxylase activity; and
   d) at least one gene encoding a polypeptide having phenol 2-monooxygenase activity; and
      (ii) growing said recombinant cell for a time sufficient to produce catechol.

3. A method for the production of cis,cis-muconate comprising:
   (i) contacting a bacterial or yeast recombinant host cell with a fermentable carbon substrate, said bacterial or yeast recombinant host cell comprising and co-expressing:
   a) at least one gene encoding a polypeptide having isochorismate synthase activity;
   b) at least one gene encoding a polypeptide having isochorismate pyruvate lyase activity;

c) at least one gene encoding a polypeptide having salicylate decarboxylase activity;
d) at least one gene encoding a polypeptide having phenol 2-monooxygenase activity; and
e) at least one gene encoding a polypeptide having catechol-1,2-dioxygenase activity; and
  (ii) growing said recombinant cell for a time sufficient to produce cis,cis-muconate.

4. A method according to claim 1, wherein the sequence of gene encoding a polypeptide having isochorismate synthase activity is as set forth in SEQ ID NO:1, 2, 3 or 4.

5. A method according to claim 1, wherein the sequence of gene encoding a polypeptide having isochorismate pyruvate lyase activity is as set forth in SEQ ID NO:5.

6. A method according to claim 1, wherein the sequence of gene encoding a polypeptide having salicylate decarboxylase activity is as set forth in SEQ ID NO:6 or 7.

7. A method according to claim 1, wherein said fermentable carbon source is selected from the group consisting of monosaccharides, oligosaccharides, polysaccharides, glycerol, carbon dioxide, methanol, formaldehyde, formate, amino acids, and carbon-containing amines.

8. A method according to claim 7 wherein said fermentable carbon source is selected from the group consisting of glucose or glycerol.

9. A method according to claim 1 wherein said recombinant host cell is selected from the group consisting of *Escherichia, Salmonella, Bacillus, Acinetobacter, Streptomyces, Corynebacterium, Methylosinus, Methylomonas, Rhodococcus, Pseudomonas, Rhodobacter, Synechocystis, Saccharomyces, Klebsiella, Zygosaccharomyces, Kluyveromyces, Candida, Hansenula, Debaryomyces, Mucor, Pichia, Torulopsis, Brevibacterium, Microbacterium, Arthrobacter, Ctirobacter*, and *Zymomonas*.

10. A method according to claim 9 wherein said recombinant host cell is a strain that overproduces chorismate or aromatic amino acids.

11. A method according to claim 1, wherein the gene encoding a polypeptide having isochorismate synthase activity is derived from *A. thaliana*.

12. A method according to claim 1, wherein the gene encoding a polypeptide having isochrosimate synthase activity is derived from *P. aeruginosa*.

13. A method according to claim 1, wherein the gene encoding a polypeptide having isochrosimate synthase activity is derived from *E. coli*.

14. A method according to claim 1, wherein the genes encoding polypeptides having isochorismate pyruvate lyase activity are derived from *P. aeruginosa*.

15. A method according to claim 1 wherein the genes encoding polypeptides having salicylate decarboxylase activity are derived from *T. moniliiforme*.

16. A method according to claim 3 wherein the gene encoding a polypeptide having phenol 2-monooxygenase activity is derived from *T. cutaneum*.

17. A method according to claim 3 wherein the gene encoding a polypeptide having phenol 2-monooxygenase activity is derived from *Pseudomonas* sp. CF600.

18. A method according to claim 3 wherein the gene encoding a polypeptide having catechol-1,2-dioxygenase activity is derived from *Pseudomonas reinekei*.

19. A method according to claim 3 wherein the gene encoding a polypeptide having catechol-1,2-dioxygenase activity is derived from *Pseudomonas putida*.

* * * * *

SEQUENCE LISTING

```
<160> NUMBER OF SEQ ID NOS: 19

<210> SEQ ID NO 1
<211> LENGTH: 1710
<212> TYPE: DNA
<213> ORGANISM: Arabidopsis thaliana

<400> SEQUENCE: 1
atggcttcac ttcaattttc ttctcagttt ctgggctcaa acactaaaac acacagctct      60
atcatttcca tctctcgtag ttactctcca actccattca ctagattctc ccgcaagaag     120
tatgagtcat gttcgatgtc tatgaatggt tgtgatggag atttcaagac gccacttggt     180
acagtggaga caaggactat gactgctgtt ttatctccgg cagccgccac tgaaaggcta     240
atctccgccg tctctgaact caaatctcaa cctccgtcgt tttcctccgg cgtcgttcgg     300
ttacaggttc caattgacca gcaaatcgga gcaattgatt ggcttcaagc cagaatgag      360 attcagcctc gctgtttctt ctctcgtcgc agtgacgttg gtcgtcccga tcttcttctc     420
gatctagcta acgagaacgg aaacggaaac ggaaacggaa cagtgtcatc tgatcgtaat     480
```

```
ctggttagcg ttgctggtat cggctctgca gtttcttcc gtgaccttga tcctttctct      540
catgacgatt ggagatccat cagaaggttt ttgtcttcaa cgtcacctct gattcgtgcc      600
tatggtggta tgcgttttga tcctaatggc aagatcgctg ttgaatggga accttttggt      660
gcattttact tttcagtccc tcaggttgag tttaatgagt ttggtggaag ttcaatgttg      720
gctgcaacta ttgcttggga tgatgaactc tcttggactc tggaaaatgc tattgaagca      780
ctccaggaga ctatgcttca gtttcttct gttgtaatga gttgagaaa cagatcttta      840 ggagtatctg tttttaagcaa gaatcatgtt cctaccaaag gagcttattt ccctgctgta      900
gagaaggctt tagagatgat taaccagaaa agttcacccc ttaacaaggt tgttcttgct      960
cgtaacagca ggataattac ggataccgac attgatccca ttgcttggct agcacagtta     1020
cagcgtgaag gcatgatgc atatcagttc tgtcttcaac cacctggtgc accagctttt     1080
atcggaaaca cgcctgagag actattccaa aggactcaat taggtgtctg cagtgaagct     1140
ttggctgcaa ctaggcctag agctgcttct agtgctcgtg atatggagat agagcgtgac     1200
ttactaacca gtccgaaaga cgacctcgag ttctctatcg tacgagagaa tataagagaa     1260
aagttaaacg gtatatgtga cagagttgtt gtcaagcctc aaaaaactgt gaggaagctt     1320
gcaagagtgc aacatctata ttctcaattg gcagggagac ttacgaagga agatgatgag     1380
tataaaatat tggctgctct gcatccaact ccagctgttt gtgggcttcc agcagaagaa     1440
gcaaggcttt tgattaagga gatagaatca ttcgatagag aatgtatgc gggacctatt     1500 ggatttttg gtggcgagga gagtgaattt gcagtcggga tcagatcagc tctagtcgaa     1560
aagggtcttg ggcattgat ctatgcgggg acagggatag tagctggaag tgacccatct     1620
tcagagtgga atgagcttga tcttaagata tctcagttca ccaagtcaat tgaatatgaa     1680
gcaacaacat ctctacaggc gattaattga                                      1710

<210> SEQ ID NO 2
<211> LENGTH: 1431
<212> TYPE: DNA
<213> ORGANISM: Pseudomonas aeruginosa

<400> SEQUENCE: 2
atgagccggc tggcgcccct gagccagtgc ctgcacgcct tgcgcggcac cttcgagcgc       60
gccatcggcc aggcgcaggc gctcgatcgt ccggtgctgg tggcggcatc gttcgagatc      120
gacccattgg acccgctgca ggtattcggt gcctgggacg accggcaaac gccctgcctg      180
tactgggaac agcccgagct ggcgttcttc gcctggggct cgcgcctgga gctgcaaggc      240
cacggcgaac agcgcttcgc ccggatcgag gaaaactggc aattgctctg cgccgacgcc      300
gtggtcgagg gcccgctggc gccgcgcctg tgcggcggat ccgcttcga tccgcgcggc      360 ccgcgcgagg aacactggca agccttcgcc gatgccagcc tgatgctcgc cggcatcacc      420
gtgctgcgcg agggcgaacg ctaccgggta ctctgccaac acctggccaa gcccggcgaa      480
gatgccctgg cctggccgc ctaccactgc tcggcgctac tgcgcctgag gcagccggcc      540
agacgccggc cctcggggcc gaccgctggc gcgcagggcg acgcttcggc gcaggagcgc      600
aggcaatggg aagccaaggt gagcgacgcg gtaagcagtg tccgccaggg acgcttcggc      660
aaggtcgtgc tggcccgcac ccaggcccgg cctctcggcg acatcgagcc gtggcaggtc      720
atcgaacacc tgcgtctgca acatgccgac gcccagctgt tcgcctgtcg ccgcggcaac      780
gcctgcttcc tcggcgcctc cccggaacgc ctggtccgca ttcgcgccgg cgaggcactc      840
acccatgccc tggccgggac catcgcccgc ggcggcgatg cccaggaaga tgcgcggctc      900
```

-continued

```
ggacaggccc tgctggacag cgccaaggac aggcacgaac accagttggt ggtggaggcg    960
atccgtacgg ccctggaacc cttcagcgag gtgctgaaaa tccccgatgc gcccggcctg   1020
aaacgactgg cgcgagtcca gcacctgaac acgccgatcc gcgcccgcct cgctgacgca   1080
ggcggcatcc tgcggctgct acaagcgctg catccgaccc ccgcgtgggg cggctaccca   1140
cgcagcgcgg cgctggacta catccgccag cacgaaggga tggaccgcgg ctggtacgcc   1200
gcgccgctgg gctggctcga cggcgaaggc aacggcgatt tcctggtggc gctgcgctcg   1260
gccctgctca cgccgggccg gggctacctg ttcgccggct gcggtctggt aggcgattcg   1320
gaaccggccc acgagtatcg cgaaacctgc cttaagctca gtgccatgcg ggaagctcta   1380
tccgccatag gcggcctgga cgaagtgccc ttgcagcgcg gcgtcgccta a             1431
```

<210> SEQ ID NO 3
<211> LENGTH: 1293
<212> TYPE: DNA
<213> ORGANISM: Escherichia coli

<400> SEQUENCE: 3

```
atgcaatcac ttactacggc gctggaaaat ctactgcgcc atttgtcgca agagattccg     60
gcgacacccg gcattcgggt tatcgatatt cctttccctc tcaaagacgc ttttgatgcc    120
ttgagctggc tggccagtca gcaaacatac ccgcaattct actggcaaca acgtaatggt    180
gatgaagaag ctgtcgtcct gggcgcgatt acccgtttta cgtcgttgga ccaggcacaa    240
cgttttcttc gccagcaccc ggaacacgcc gacttacgca tttgggggct gaatgctttt    300
gacccgtcgc agggcaattt acttttaccc cgcctggaat ggcgacgctg tggcggtaaa    360
gccacgctgc ggctgacgct attcagcgaa agctcccttc agcacgatgc gattcaggca    420
aaagaattta tcgccacact ggtgagtatc aagcccttgc ctgggttaca tttaaccacc    480
acgcgagaac aacactggcc ggacaaaacg ggctggacgc aattaatcga actggcaacg    540
aaaaccatcg ccgaaggtga gctcgacaaa gtggtgctcg ctcgggcaac tgacctgcat    600
ttcgcaagtc cggtcaacgc ggcggcgatg atggctgcca gtcgtcgact gaatctgaat    660
tgctaccatt tttacatggc ctttgatggc gaaaatgctt tcttggctc ttcaccggaa    720
cggttatggc ggcggcgtga caaagcgctg cgtactgaag cgctggcggg aacagtagca    780
aataatcctg atgataagca ggcgcagcag ttaggagagt ggctgatggc ggatgataaa    840
aaccagcgcg agaacatgct ggtggtggaa gatatctgtc aacgattaca ggccgatacc    900
cagacgctgg atgttttacc gccgcaggta ctgcgtctgc gtaaagtgca gcatcttcgc    960
cgctgtatct ggacttcact caacaaagcg gatgatgtga tctgtttaca tcagttgcag   1020
ccaacggcag cagttgctgg cttaccgcgc gatctgcgc gacagtttat cgcccgtcac   1080
gaaccgttca cccgagaatg gtacgccggt tctgcgggct atctctcatt acaacaaagc   1140
gaattctgcg tttccctgcg ctcagcaaaa attagcggca atgtcgtgcg attatatgct   1200
ggcgcgggca ttgtccgtgg ttccgacccc gagcaagagt ggcaggaaat cgacaacaaa   1260
gcggcagggc tgcgtacttt attacaaatg gaa                                1293
```

<210> SEQ ID NO 4
<211> LENGTH: 1173
<212> TYPE: DNA
<213> ORGANISM: Escherichia coli

<400> SEQUENCE: 4

-continued

| | |
|---|---|
| atggatacgt cactggctga ggaagtacag cagaccatgg caacacttgc gcccaatcgc | 60 |
| tttttctta tgtcgccgta ccgcagtttt acgacgtcag gatgtttcgc ccgcttcgat | 120 |
| gaaccggctg tgaacgggga ttcgcccgac agtcccttcc agcaaaaact cgccgcgctg | 180 |
| tttgccgatg ccaaagcgca gggcatcaaa atccggtga tggtcggggc gattcccttc | 240 |
| gatccacgtc agccttcgtc gctgtatatt cctgaatcct ggcagtcgtt ctcccgtcag | 300 |
| gaaaaacaag cttccgcacg ccgtttcacc cgcagccagt cgctgaatgt ggtggaacgc | 360 |
| caggcaattc cggagcaaac cacgtttgaa cagatggttg cccgcgccgc cgcacttacc | 420 |
| gccacgccgc aggtcgacaa agtggtgttg tcacggttga ttgatatcac cactgacgcc | 480 |
| gccattgata gtggcgtatt gctggaacgg ttgattgcgc aaaacccggt tagttacaac | 540 |
| ttccatgttc cgctggctga tggtggcgtc ctgctggggg ccagcccgga actgctgcta | 600 |
| cgtaaagacg gcgagcgttt tagctccatt ccgttagccg gttccgcgcg tcgtcagccg | 660 |
| gatgaagtgc tcgatcgcga agcaggtaat cgtctgctgg cgtcagaaaa agatcgccat | 720 |
| gaacatgaac tggtgactca ggcgatgaaa gaggtactgc gcgaacgcag tagtgagtta | 780 |
| cacgttcctt cttctccaca gctgatcacc acgccgacgc tgtggcatct cgcaactccc | 840 |
| tttgaaggta aagcgaattc gcaagaaaac gcactgactc tggcctgtct gctgcatccg | 900 |
| accccgcgc tgagcggttt cccgcatcag gccgcgaccc aggttattgc tgaactggaa | 960 |
| ccgttcgacc gcgaactgtt tggcggcatt gtgggttggt gtgacagcga aggtaacggc | 1020 |
| gaatgggtgg tgaccatccg ctgcgcgaag ctgcgggaaa atcaggtgcg tctgtttgcc | 1080 |
| ggagcgggga ttgtgcctgc gtcgtcaccg ttgggtgagt ggcgcgaaac aggcgtcaaa | 1140 |
| cttttctacca tgttgaacgt ttttggattg cat | 1173 |

<210> SEQ ID NO 5
<211> LENGTH: 309
<212> TYPE: DNA
<213> ORGANISM: Pseudomonas aeruginosa

<400> SEQUENCE: 5

| | |
|---|---|
| atgatgaaaa ctcccgaaga ctgcaccggc ctggcggaca tccgcgaggc catcgaccgg | 60 |
| atcgacctgg atatcgtcca ggccctcggc cgccgcatgg actacgtcaa ggcggcgtcg | 120 |
| cgcttcaagg ccagcgaggc ggcgattccg gcgcccgagc gggtcgccgc gatgctcccc | 180 |
| gagcgcgccc gctgggccga ggaaaacgga ctcgacgcgc ccttcgtcga gggactgttc | 240 |
| gcgcagatca tccactggta catcgccgag cagatcaagt actggcgcca gacacggggt | 300 |
| gccgcataa | 309 |

<210> SEQ ID NO 6
<211> LENGTH: 1053
<212> TYPE: DNA
<213> ORGANISM: Trichosporon moniliiforme

<400> SEQUENCE: 6

| | |
|---|---|
| atgcgcggaa aggtttctct cgaggaggcg ttcgagcttc ccaagttcgc tgcccagacc | 60 |
| aaggagaagg ccgagctcta catcgccccc aacaaccgcg accggtactt tgaggagatt | 120 |
| ctcaacccgt gcggcaaccg tctcgagctt tcgaacaagc acggtatcgg ctacaccatc | 180 |
| tactctatct actcgcctgg tccgcaggga tggaccgagc gcgccgagtg tgaggagtac | 240 |
| gcgcgcgagt gcaacgacta catctcgggc gagattgcca atcacaagga ccggatgggt | 300 |
| gcctttgccg ctctgtcgat gcacgacccc aagcaggcgt ccgaggagct tacccgctgc | 360 |

-continued

```
gttaaagagc tcggtttcct cggcgcgctc gtcaacgacg tgcagcacgc cggacccgaa      420
ggcgagaccc acatcttcta cgaccagccc gagtgggaca tcttctggca gacttgcgtc      480
gatctcgacg ttccattcta cctccacccc gagcctccct tcggctcgta cctccgcaac      540
cagtacgagg gacgcaagta ccttattggt cctcccgtgt cttttgccaa cggcgtctcg      600
ctccacgtcc tcggcatgat cgtcaacggt gtctttgacc gcttccccaa gctcaaggtc      660
atcctcggcc accttggcga gcacattccc ggagacttct ggcgcatcga gcactggttc      720
gagcactgct cccgccctct cgccaagtcg cgcggagacg tcttcgctga agcccctc       780 ctccactact tccgcaacaa catctggctc accacctcgg gcaacttctc caccgagact      840
ctcaagttct gcgtcgagca cgtcggcgcc gagcgcatcc tcttctccgt cgactcgcct      900
tacgagcaca tcgacgtcgg atgcggatgg tacgacgaca acgccaaggc tatcatggag      960
gccgttggcg gtgagaaggc ctacaaggac attggccgtg acaacgccaa gaagctcttc     1020
aagctcggca agttctacga ctcggaggct tag                                  1053
```

<210> SEQ ID NO 7
<211> LENGTH: 1053
<212> TYPE: DNA
<213> ORGANISM: Trichosporon moniliiforme

<400> SEQUENCE: 7

```
atgcgtggta agttagcct ggaagaagca tttgaactgc cgaaatttgc agcacagacc       60
aaagaaaaag ccgaactgta tattgcaccg aataatcgcg atcgctattt tgaagaaatt      120
ctgaatccgt gtggtaatcg tctggaactg agcaataaac atggtattgg ctataccatc      180
tatagcatct attcaccggg tccgcagggt tggaccgaac gtgcagaatg tgaagaatat      240
gcacgtgaat gcaacgatta tatcagcggt gaaattgcca atcacaaaga tcgtatgggt      300
gcatttgcag ccctgagcat gcatgatccg aaacaggcaa gcgaagaact gacccgttgt      360
gttaaagaac tgggttttct gggtgcactg gttaatgatg ttcagcatgc aggtccggaa      420
ggtgaaaccc atatcttttta tgatcagccc gaatgggata tcttttggca gacctgtgtt      480
gatctggatg ttccgtttta tctgcatccg gaaccgcctt ttggtagcta tctgcgtaat      540
cagtatgaag gtcgcaaata tctgattggt ccgcctgtta gctttgcaaa tggtgttagc      600
ctgcatgttc tgggtatgat tgttaatggt gtgtttgatc gttttccgaa actgaaagtt      660
attctgggtc atcttgggtga acatattccg ggtgatttt ggcgtattga cattggttt       720 gaacactgta gccgtccgct ggcaaaaagc cgtggtgatg tttttgcaga aaaaccgctg      780
ctgcattatt ttcgcaataa catttggctg accacgagcg gcaattttag caccgaaacc      840
ctgaaatttt gcgttgaaca tgttggtgca gaacgcattc tgtttagcgt tgatagcccg      900
tatgaacata tcgatgttgg ttgtggttgg tatgatgata atgccaaagc aattatggaa      960
gccgttggtg gtgaaaaagc ctataaagat attggtcgcg acaacgcgaa aaaactgttt     1020
aaactgggca aattctatga cagcgaagcc taa                                  1053
```

<210> SEQ ID NO 8
<211> LENGTH: 44
<212> TYPE: DNA
<213> ORGANISM: Artificial Sequence
<220> FEATURE:
<223> OTHER INFORMATION: Primer

<400> SEQUENCE: 8
ataggatcca ggaggataaa taatggcttc acttcaattt tctt         44

<210> SEQ ID NO 9
<211> LENGTH: 34
<212> TYPE: DNA
<213> ORGANISM: artificial sequence
<220> FEATURE:
<223> OTHER INFORMATION: Primer

<400> SEQUENCE: 9
atttctagat taattaatcg cctgtagaga tgtt         34

<210> SEQ ID NO 10
<211> LENGTH: 44
<212> TYPE: DNA
<213> ORGANISM: Artificial Sequence
<220> FEATURE:
<223> OTHER INFORMATION: Primer

<400> SEQUENCE: 10
ataggatcca ggaggataaa taatgagccg gctggcgccc ctga         44

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
atttctagat taggcgacgc cgcgctgcaa g         31

<210> SEQ ID NO 12
<211> LENGTH: 43
<212> TYPE: DNA
<213> ORGANISM: Artificial Sequence
<220> FEATURE:
<223> OTHER INFORMATION: Primer

<400> SEQUENCE: 12
ataggatcca ggaggataaa taatgcaatc acttactacg gcg         43

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
atttctagat tattccattt gtaataaagt acgcag         36

<210> SEQ ID NO 14
<211> LENGTH: 42
<212> TYPE: DNA
<213> ORGANISM: Artificial Sequence
<220> FEATURE:
<223> OTHER INFORMATION: Primer

<400> SEQUENCE: 14
ataggatcca ggaggataaa taatggatac gtcactggct ga         42

<210> SEQ ID NO 15
<211> LENGTH: 30
<212> TYPE: DNA
<213> ORGANISM: Artificial Sequence

```
<220> FEATURE:
<223> OTHER INFORMATION: Primer

<400> SEQUENCE: 15
atttctagat taatgcaatc caaaaacgtt                                      30

<210> SEQ ID NO 16
<211> LENGTH: 43
<212> TYPE: DNA
<213> ORGANISM: Artificial Sequence
<220> FEATURE:
<223> OTHER INFORMATION: Primer

<400> SEQUENCE: 16
ataccatgga ggaggataaa taatgatgaa aactcccgaa gac                       43

<210> SEQ ID NO 17
<211> LENGTH: 31
<212> TYPE: DNA
<213> ORGANISM: Artificial Sequence
<220> FEATURE:
<223> OTHER INFORMATION: Primer

<400> SEQUENCE: 17
attgaattct tatgcggcac cccgtgtctg g                                    31

<210> SEQ ID NO 18
<211> LENGTH: 43
<212> TYPE: DNA
<213> ORGANISM: Artificial Sequence
<220> FEATURE:
<223> OTHER INFORMATION: Primer

<400> SEQUENCE: 18
ataccatgga ggaggataaa taatgcgtgg taaagttagc ctg                       43

<210> SEQ ID NO 19
<211> LENGTH: 31
<212> TYPE: DNA
<213> ORGANISM: Artificial Sequence
<220> FEATURE:
<223> OTHER INFORMATION: Primer

<400> SEQUENCE: 19
attgaattct taggcttcgc tgtcatagaa t                                    31
```